(12) United States Patent
Fischer et al.

(10) Patent No.: US 6,267,990 B1
(45) Date of Patent: Jul. 31, 2001

(54) CONTROLLED-RELEASE PHARMACEUTICAL PREPARATION COMPRISING AN ACE INHIBITOR AS ACTIVE INGREDIENT

(75) Inventors: Wilfried Fischer; Karin Klokkers; Renate Oppelt, all of Holzkirchen (DE)

(73) Assignee: Hexal AG, Holzkirchen (DE)

( * ) Notice: Subject to any disclaimer, the term of this patent is extended or adjusted under 35 U.S.C. 154(b) by 0 days.

(21) Appl. No.: 09/460,055

(22) Filed: Dec. 13, 1999

Related U.S. Application Data

(63) Continuation of application No. PCT/EP98/03536, filed on Jun. 12, 1998.

(30) Foreign Application Priority Data

Jun. 12, 1997 (DE) .............................................. 197 24 696

(51) Int. Cl.[7] ..................................................... A61K 9/16
(52) U.S. Cl. ......................... 424/490; 424/493; 424/494; 424/498
(58) Field of Search .................................... 424/456, 458, 424/461, 472, 490, 493, 494, 498

(56) References Cited

U.S. PATENT DOCUMENTS 5,158,777 * 10/1992 Abramowitz et al. ............... 424/458
5,876,754 * 3/1999 Wunderlich et al. ................ 424/489

FOREIGN PATENT DOCUMENTS 44 31 832 A1   3/1996  (DE) .
WO96/29994    10/1996  (WO) .

OTHER PUBLICATIONS

Translation of International Preliminary Examination Report for PCT/EP98/03536.
International Search Report for PCT/EP98/03536 dated Oct. 6, 1998.

* cited by examiner

*Primary Examiner*—Thurman K. Page
*Assistant Examiner*—S. Tran
(74) *Attorney, Agent, or Firm*—Marshall, O'Toole, Gerstein, Murray & Borun

(57) ABSTRACT

The invention relates to a pharmaceutical preparation which comprises or consists of the following components:
  (i) an initial dose of active ingredient, which is provided by the active ingredient together with optional excipients,
  (ii) a first delayed-release type of pellet, in which the active ingredient and optional excipients are covered with a coating, and
  (iii) a second delayed-release type of pellet, in which the active ingredient and optional excipients are again covered with a coating,
wherein the active ingredient is an ACE inhibitor, and
wherein the amounts of the coatings according to (ii) and (iii) are present in a ratio, based on weight, within the range of from 1:2 to 1:7.

36 Claims, 4 Drawing Sheets

Figure 1:
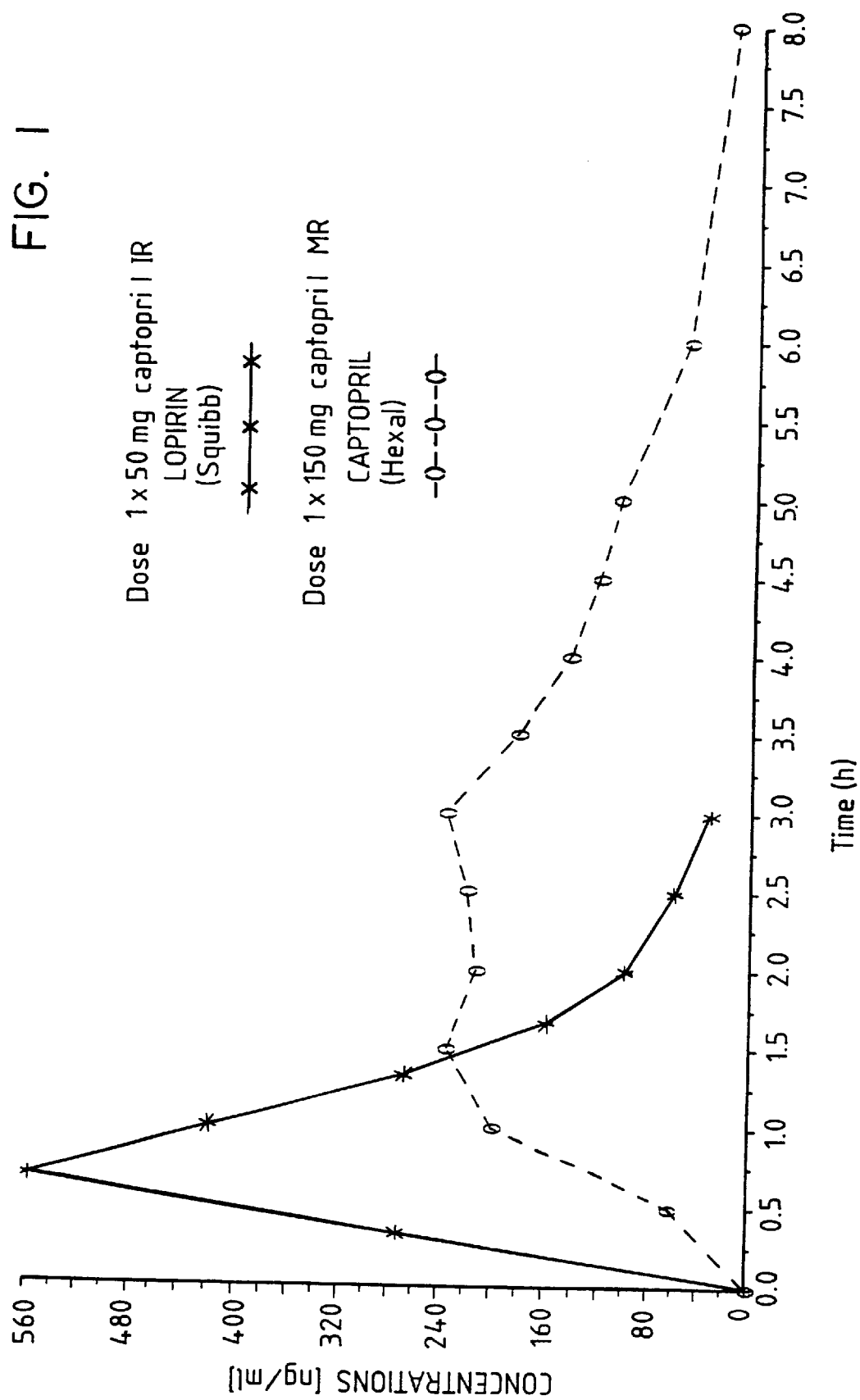

Mean captopril concentrations (left axis, open symbols) and mean ACE activities q(right axis, filled symbols) and average curve fits after PK/PD data analysis.
□,■ -Reference Product
○,● -Test Product

CONTROLLED-RELEASE PHARMACEUTICAL PREPARATION COMPRISING AN ACE INHIBITOR AS ACTIVE INGREDIENT

This is a continuation of International Application No. PCT/EP98/03536 filed Jun. 12, 1998, the entire disclosure of which is incorporated herein by reference.

The present invention relates to a pharmaceutical preparation with which it is possible to achieve improved release of active ingredient as a function of time and of the pH value of the surroundings. The invention relates especially to such a preparation comprising an ACE (angiotensin converting enzyme) inhibitor as active ingredient, especially comprising captopril.

Slow-release pharmaceutical dosage forms for the controlled and delayed release of captopril are known. For example, U.S. Pat. No. 5,158,777 describes a composition in which a portion of the active ingredient (captopril) is released immediately and a second portion is released in a delayed manner. That is achieved, according to Example 2, by the provision of two different types of pellet, of which one type of pellet, containing active ingredient, is uncoated, while the other type, containing active ingredient, has a core comprising, inter alia, captopril and ascobic acid, the core being coated with a methacrylic acid polymer (EUDRAGIT® RS) which causes the active ingredient to be released in a delayed manner.

Other slow-release forms of captopril include, for example, according to U.S. Pat. No. 4,666,705 an uncoated tablet containing an acrylic acid polymer; according to U.S. Pat. No. 5,738,850 a preparation containing captopril in combination with chitosan; and according to U.S. Pat. No. 4,756,911 a coated tablet comprising a core containing, for example, captopril as active ingredient (column 4, line 57), one or more water-soluble or water-swellable primary hydrocolloidal swelling agents containing methoxy groups, one or more secondary hydrocolloidal swelling agents, one or more non-swellable binders and/or waxes, and one or more lubricants.

It has been found, however, that the prior art is in need of improvement in that the active ingredient is released prematurely according to the prior art and thus leads to a therapeutic plasma level that has too short a duration. In addition, in some slow-release forms the coatings may not have dissolved sufficiently to release the active ingredient when the tablet has reached the intestine so that the active ingredient is excreted before it is absorbed from the stomach/intestinal tract, since no further absorption takes place in the large intestine.

Investigations underlying the invention have shown that although formulations according to the prior art exhibit retarding effects in vitro, it is not possible in vivo to obtain a constant and therapeutically effective blood level concentration over a prolonged period, or to achieve prolonged ACE inhibition.

The problem underlying the invention is to provide a pharmaceutical preparation, especially a preparation comprising an ACE inhibitor as active ingredient, for example comprising captopril, that permits controlled release of the active ingredient, especially in the case of a single dose, and thus ensures over a prolonged period a therapeutically effective blood level with minimal variations in the blood level concentration, and that meets the requirement that the action should begin immediately and, furthermore, that permits prolonged ACE inhibition.

To that end there is provided according to the invention a pharmaceutical preparation which comprises or consists of the following components:

(i) an initial dose of active ingredient, which is provided by the active ingredient as desired in the form of a powder, granules and/or pellets, in each case together with optional excipients, (ii) a first delayed-release type of pellet, in which the active ingredient and optional excipients are covered with a coating, and (iii) a second delayed-release type of pellet, in which the active ingredient and optional excipients are again covered with a coating, wherein the active ingredient is an ACE inhibitor, and wherein the amounts of the coatings according to (ii) and (iii) are present in a ratio, based on weight, within the range of from 1:2 to 1:7.

With the preparation according to the invention it has been found, with captopril as active ingredient, that blood level concentrations with extremely small variations can be established in vivo and, moreover, that the action of the medicament begins almost immediately. Surprisingly, the active ingredient is released from the preparation according to the invention in such a manner that pronounced blood level peaks at the beginning are avoided and yet therapeutically effective blood concentrations are maintained over a long period of time. Above all it has been found, surprisingly, that ACE inhibition of above average duration can be achieved.

In the preparation according to the invention, the amounts of the coatings according to (ii) and (iii) may be present in a ratio, based on weight, of approximately 1:5.

The active ingredient is, therefore, an ACE (angiotensin converting enzyme) inhibitor, especially captopril, moexipril, perindopril, quinapril, ramipril, spirapril, tandolapril, mixtures thereof and/or their pharmaceutically acceptable salts, for example hydrochlorides, for example perindopril erbumine.

The active ingredient content of the initial dose may be from 5 to 30% by weight of the total active ingredient content.

In the initial dose, the active ingredient may be in the form of a powder, granules and/or in the form of a pellet, it being possible for granules and pellets to contain customary excipients.

Pellets of the first and second delayed-release types can be obtained by providing pellets which may have been prepared for an initial dose with the respective coating.

The coating for the first and second types of delayed-release pellet may be a coating that is resistant to qastic juices, especially based on polymethacrylic acid, more especially on EUDRAGIT® S. In a preferred embodiment, the same coating material is chosen for the first and second types of delayed-release pellet.

In a preferred embodiment, the coating for the first and second types of delayed-release pellet has, apart from polymethacrylic acid, no other component of equal or greater acidity.

The coating for the first and/or second type(s) of delayed-release pellet may comprise customary film-forming agents and/or excipients, especially dibutyl phthalate, polyethylene glycol, triethyl citrate (CITROFLEX®), ethyl cellulose (AQUACOAT®) titanium dioxide and/or hydroxypropylmethyl cellulose. Microcrystalline cellulose and/or lactose may come into consideration as excipients.

The ratio by weight of initial dose to first type of delayed-release pellet to second type of delayed-release pellet may be within the range of from 1:1:1 to 1:10:10 and may be especially approximately 1: approximately 1: approximately 2.

The preparation according to the invention can be characterised by the following proportions by weight:

initial dose: from 10 to 30% by weight, first type of delayed-release pellet: from 20 to 40% by weight, and second type of delayed-release pellet: from 40 to 60% by weight, the sum of all three components being 100% by weight; it can be characterised especially by initial dose: approximately 22.9% by weight, first type of delayed-release pellet: approximately 25.8% by weight, and second type of delayed-release pellet: approximately 51.3% by weight, the sum of all three components being 100% by weight.

The preparation according to the invention may be in the form of a capsule, especially a gelatin capsule, the capsule comprising all three components. Such a capsule may comprise an amount of active ingredient required for a daily dose or for a single dose. For example, a capsule may comprise an amount of captopril required for the daily dose or single dose, especially in the range of from 25 to 300 mg, more especially from 50 to 200 mg and very especially from 75 to 150 mg.

The initial dose of captopril, based on a daily dose or a single dose, may be from 5 to 30 mg.

The active ingredient content of the pellets may be from 10 to 50%, it being possible to use customary excipients for pellet formation, such as microcrystalline cellulose and/or lactose, and it being possible for the pellets of the three components to have different active ingredient contents.

The ratio of the active ingredient contents is from 1:3:3 to 1:10:10, especially 1:2.5:4.

Figure 2:
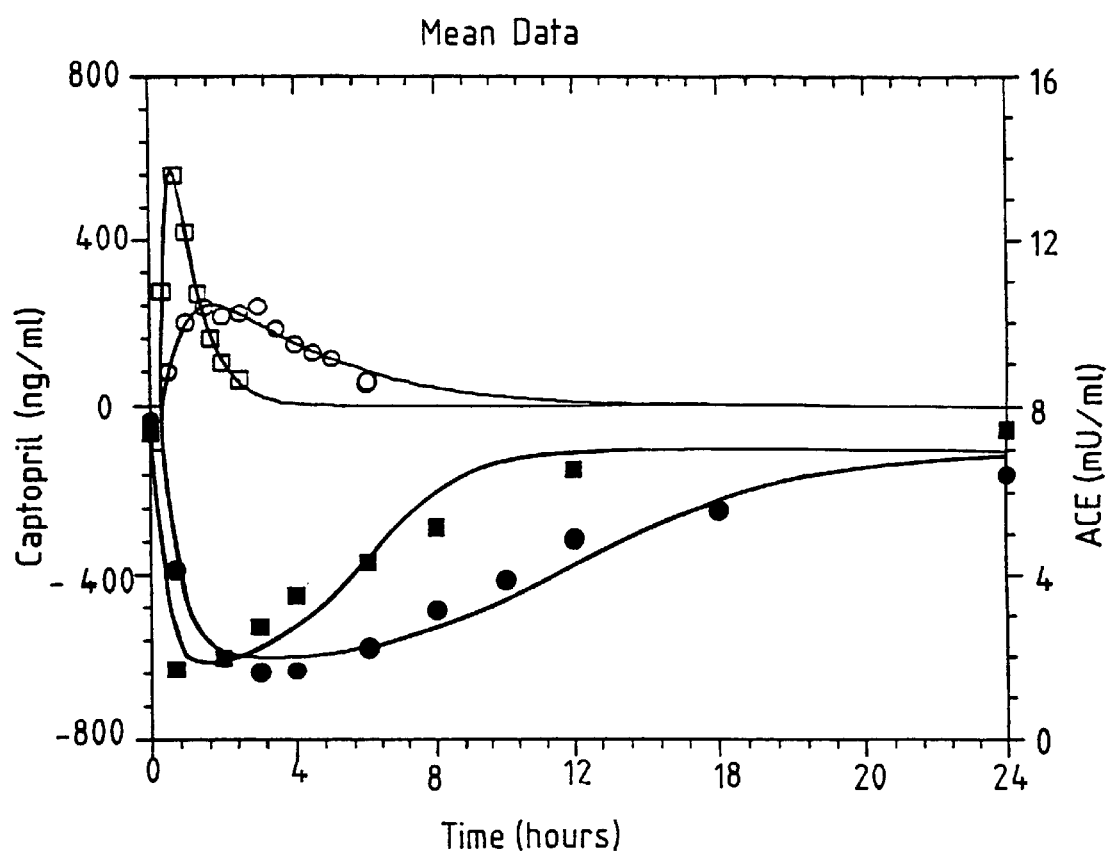
Figure 3:
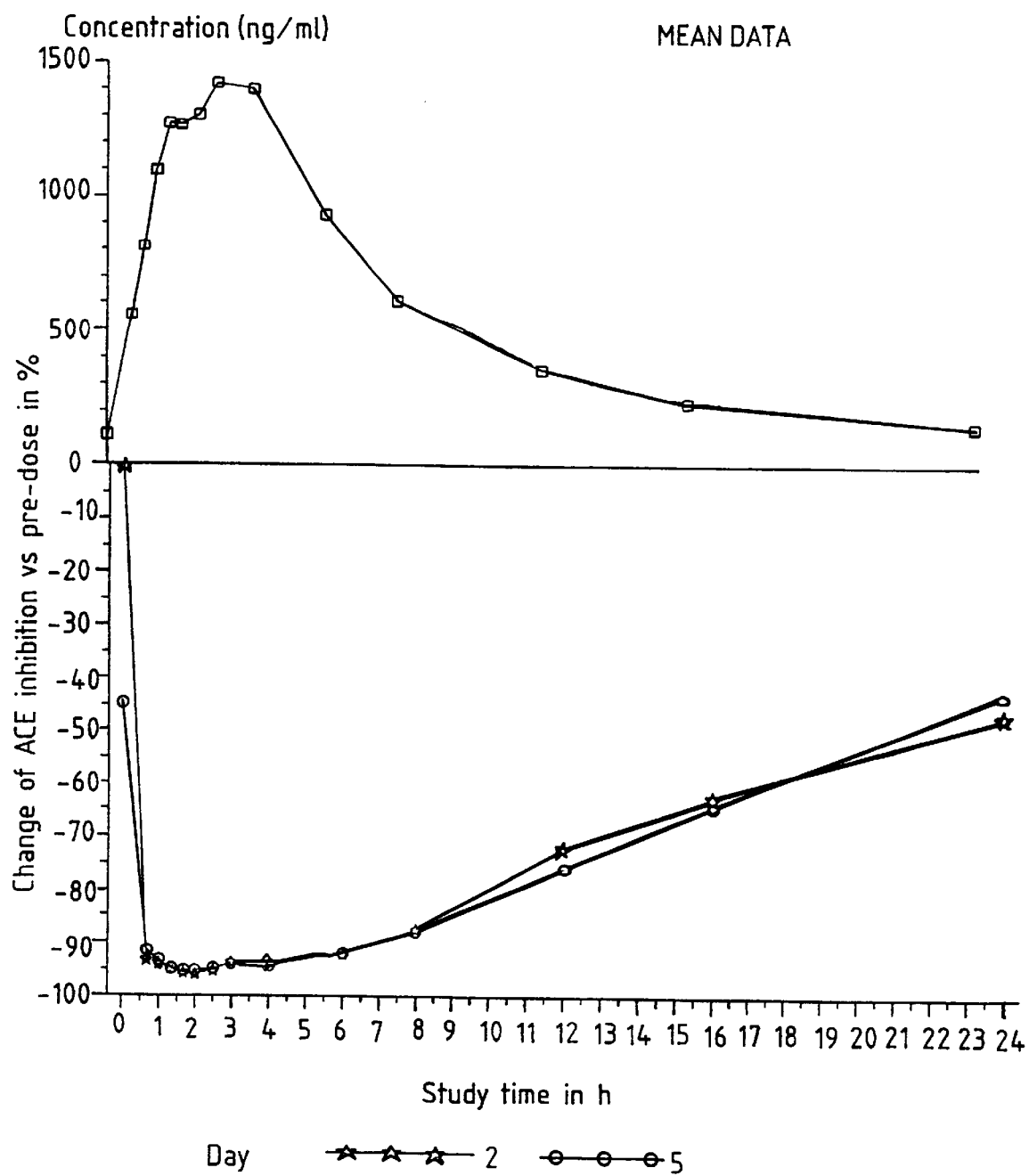
Figure 4:
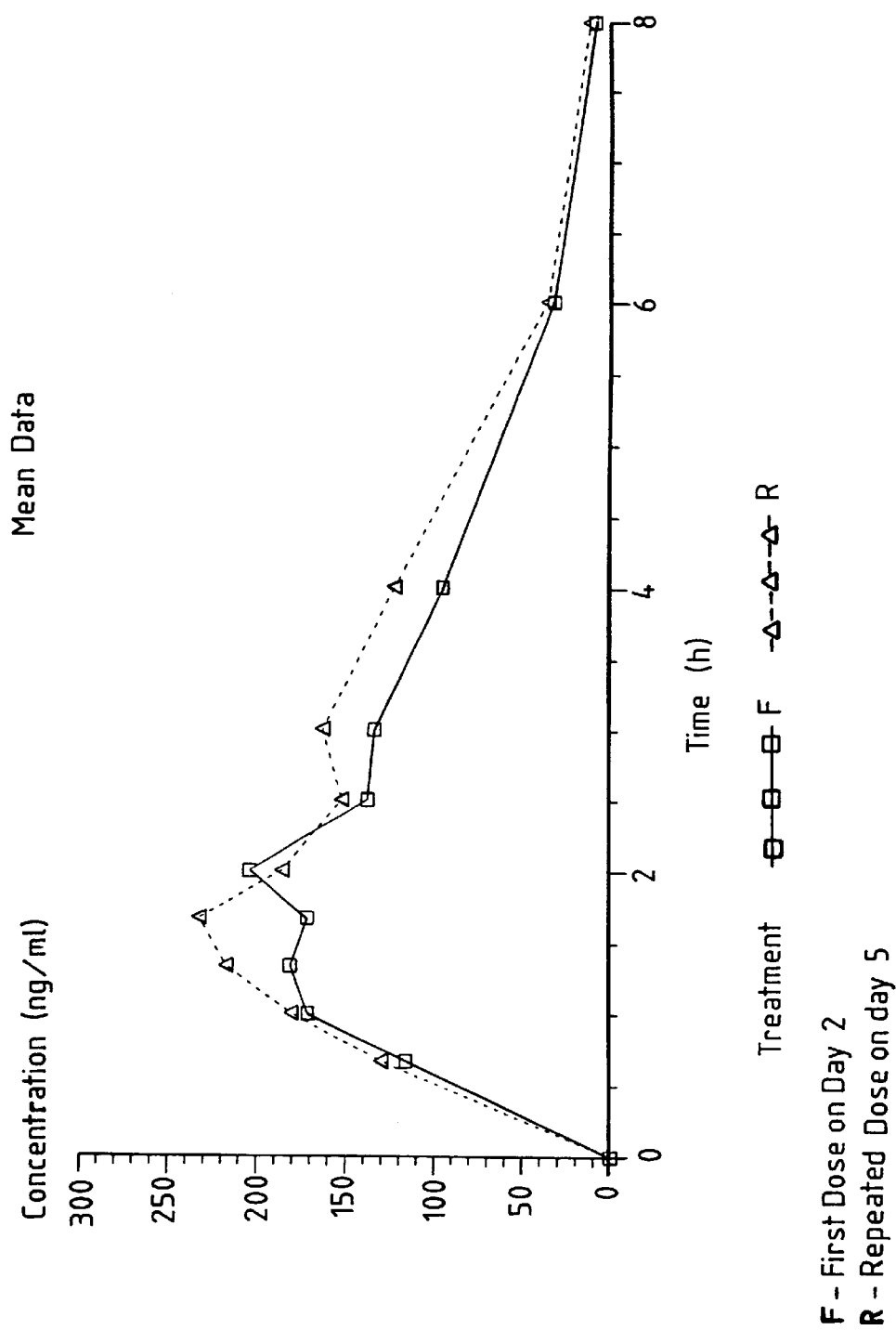

The invention is explained in greater detail below with reference to Examples and Figures. In the Figures FIG. 1 shows the retarding effect of a captopril capsule according to Example 1 in comparison with a rapid-release captopril tablet;

FIGS. 2 and 4 shows a plasma captopril level in relation to the ACE inhibition corresponding to FIG. 1; and FIG. 3 shows a plasma captopril level in relation to the ACE inhibition corresponding to Example 2.

EXAMPLE 1

A) Preparation

The following three types of pellet were provided for captopril slow-release capsules:

Pellet 1; the composition was as follows:

| captopril | 5 mg |
| Avicel (microcrystalline cellulose) | 3 mg |
| Tablettose | 2 mg |

Pellet 2; 700 9 of pellets of type 1 were first film-coated with 40.48 g of OPADRY II and 250 g of water. The solution for a second film coating had the following composition:

| EUDRAGIT ® S 100 | 62.5 g |
| dibutyl phthalate | 6.25 g |

-continued

| 96% ethanol | 350.00 g |
| purified water | 87.5 g |

Pellet 3; 700 g of pellets of type 1 were provided with an initial film coating of 40.48 g of OPADRY II and 250 g of water. The solution for a second film coating had the following composition:

| EUDRAGIT ® S 100 | 192.5 g |
| dibutyl phthalate | 19.25 g |
| 96% ethanol | 1078 g |
| purified water | 269.5 g |

For the preparation of captopril slow-release capsules, 100 mg of pellets of type 1, 700 mg of pellets of type 2 and 700 mg of pellets of type 3 were introduced into a gelatin capsule. This produced a total active ingredient concentration of captopril of 150 mg.

B) Pharmacokinetic and Pharmacodynamic Tests

Plasma levels and ACE inhibition were determined in an open cross-over study based on individual doses. The test subjects received either a capsule according to the invention comprising 150 mg of captopril or a reference product comprising 50 mg of captopril. FIG. 1 shows the retarding effect of the captopril capsule according to the invention in comparison with a rapid-release captopril tablet. FIG. 2 shows plasma captopril levels in relation to ACE inhibition.

Example 2

Preparation

The following three components were provided for captopril slow-release capsules:

Component 1 (initial dose):

| captopril (powder) | 20 mg |

Component 2 (first type of delayed-release pellet):

| captopril | 50 mg |
| microcrystalline cellulose | 49.37 mg |
| Opadry, white, consisting of lactose H$_2$O | 2.07 mg |
| hydroxypropylmethyl cellulose | 1.61 mg |
| titanium dioxide | 1.49 mg |
| Macrogol 4000 | 0.58 mg |
| EUDRAGIT ® S 100 | 6.13 mg |
| dibutyl phthalate | 0.61 mg |

Component 3 (second type of delayed-release pellet):

| captopril | 80 mg |
| microcrystalline cellulose | 81.64 mg |
| Opadry, white, consisting of lactose H$_2$O | 3.37 mg |
| hydroxypropylmethyl cellulose | 2.62 mg |
| titanium dioxide | 2.43 mg |

| | |
|---|---|
| Macrogol 4000 | 0.93 mg |
| EUDRAGIT® S 100 | 50 mg |
| dibutyl phthalate | 5 mg |

The active ingredient concentration of captopril per capsule is 150 mg.

Example 3

The following three components were provided for captopril slow-release capsules:

Component 1 (initial dose): 50% captopril

| | |
|---|---|
| captopril | 20 mg |
| microcrystalline cellulose | 20.12 mg |

Component 2 (first type of delayed-release pellet): 50% captopril

| | |
|---|---|
| captopril | 50 mg |
| microcrystalline cellulose | 49.36 mg |
| Opadry, white, consisting of lactose H₂O | 2.06 mg |
| hydroxypropylmethyl cellulose | 1.61 mg |
| titanium dioxide | 1.50 mg |
| Macrogol 4000 | 0.58 mg |
| EUDRAGIT® S 100 | 6.14 mg |
| dibutyl phthalate | 0.61 mg |

Component 3 (second type of delayed-release pellet): 50% captopril

| | |
|---|---|
| captopril | 80 mg |
| microcrystalline cellulose | 81.64 mg |
| Opadry, white, consisting of lactose H₂O | 3.37 mg |
| hydroxypropylmethyl cellulose | 2.62 mg |
| titanium dioxide | 2.43 mg |
| Macrogol 400 | 0.93 mg |
| EUDRAGIT® S 100 | 50 mg |
| dibutyl phthalate | 5 mg |

In this Example too, the active ingredient concentration per capsule is 150 mg of captopril.

Example 4

Composition of the captopril slow-release capsules:

Component 1 (initial dose):

| | |
|---|---|
| captopril | 20 mg |
| lactose D80 | 56 mg |
| microcrystalline cellulose | 24 mg | component 2 (first type of delayed-release pellet):

| | |
|---|---|
| captopril pellets 50% | 99.93 mg |
| Opadry | 5.78 mg |
| EUDRAGIT® S 100 | 6.17 mg |

| | |
|---|---|
| dibutyl phthalate | 0.62 mg |
| water | 44.33 mg |
| 96% ethanol | 34.54 mg | component 3 (second type of delayed-release pellet):

| | |
|---|---|
| captopril pellets 50% | 160.21 mg |
| Opadry | 9.27 mg |
| EUDRAGIT® S 100 | 49.56 mg |
| dibutyl phthalate | 4.96 mg |
| water | 126.61 mg |
| 96% ethanol | 277.56 mg | the total active ingredient concentration of a slow-release capsule is 150 mg of captopril.

What is claimed is:

1. Pharmaceutical preparation which comprises the following components:
   (i) an initial dose of an active ingredient optionally including at least one excipient,
   (ii) a first delayed-release pellet, in which the active ingredient and optional excipient(s) are covered with a coating, and
   (iii) a second delayed-release pellet, in which the active ingredient and optional excipient(s) are covered with a coating,
   wherein the active ingredient is an ACE (angiotensin converting enzyme) inhibitor, and
   wherein the amounts of the coatings according to (ii) and (iii) are present in a ratio, based on weight, within the range of from 1:2 to 1:7.

2. Preparation according to claim 1, wherein the amounts of the coatings according to (ii) and (iii) are present in a ratio, based on weight, of approximately 1:5.

3. Preparation according to claim 1, wherein the active ingredient is selected from the group consisting of ACE inhibitors captopril, moexipril, perindopril, quinapril, ramipril, spirapril, tandolapril, mixtures thereof and their pharmaceutically acceptable salts.

4. Preparation according to claim 1, wherein the active ingredient in the initial dose is in the form of at least one of a powder, granules and pellets.

5. Preparation according to claim 1, wherein at least one of the pellets of the first delayed-release pellet and the pellets of the second delayed-release pellet have been obtained by providing the initial dose in the form of pellets with the respective coating.

6. Preparation according to claim 1, wherein the coating for at least one of the first and second delayed-release pellets is a coating that is resistant to gastric juices.

7. Preparation according to claim 1, wherein the coating comprises at least one film-forming agent or excipient.

8. Preparation according to claim 1, wherein the active ingredient content of the initial dose of active ingredient is from 5% to 30% by weight of the total active ingredient content of the preparation.

9. Preparation according to claim 1, wherein the ratio (based on weight) of (i):(ii):(iii) is in the range of from 1:1:1 to 1:10:10.

10. Preparation according to claim 1, wherein the active ingredient content of the initial dose of at least one of the first delayed-release pellets and of the second delayed-release pellets is from 10 to 50% (based on weight).

11. Preparation according to claim 1, wherein the ratio of the contents of the active ingredient of initial dose: first delayed-release pellets: second delayed-release pellets is in the range of from 1:3:3 to 1:10:10.

12. Preparation according to claim 1, wherein
the initial dose comprises from 10% to 30% by weight,
the first delayed-release pellet comprises from 20% to 40% by weight, and
the second delayed-release pellet comprises from 40% to 60% by weight,
the sum of all three components being 100% by weight.

13. Preparation according to claim 1, wherein
the initial dose comprises approximately 22.9% by weight,
the first delayed-release pellet comprises approximately 25.8% by weight, and
the second delayed-release pellet comprises approximately 51.3% by weight,
the sum of all three components being 100% by weight.

14. Preparation according to claim 1 in the form of a capsule comprising all three components.

15. Preparation according to claim 14, wherein the capsule comprises an amount of active ingredient required for a daily dose or for a single dose.

16. Preparation according to claim 14 wherein the capsule comprises an amount of captopril required for the daily dose or single dose.

17. Preparation according to claim 1, wherein based on a daily dose or a single dose, captopril is the active ingredient, and the initial dose is from 5 mg to 30 mg.

18. Preparation according to claim 1, comprising at least one of microcrystalline cellulose and lactose as an excipient.

19. Preparation according to claim 1 consisting of components (i), (ii), and (iii).

20. Preparation according to claim 3, wherein the active ingredient is in the form of a hydrochloride salt.

21. Preparation according to claim 20, wherein the active ingredient is perindopril erbumine.

22. Preparation according to claim 6, wherein the coating for at least one of the first and second delayed-release pellets is based on polymethacrylic acid.

23. Preparation according to claim, 22, wherein the coating for at least one of the first and second types of delayed-release pellet is poly(methacrylic acid, methyl methacrylate).

24. Preparation according to claim 22, wherein the coating has, apart from polymethacrylic acid, no other component of equal or greater acidity.

25. Preparation according to claim 7, wherein said film-forming agent or excipient is at least one member selected from the group consisting of dibutyl phthalate, polyethylene glycol, triethyl citrate, ethyl cellulose, titanium dioxide, and hydroxypropylmethyl cellulose.

26. Preparation according to claim 25, wherein said film-forrning agent or excipient is triethyl citrate or ethyl cellulose.

27. Preparation according to claim 9, wherein said ratio of components (i):(ii):(iii) is about 1:1:2.

28. Preparation according to claim 10, wherein the initial dose is in the form of pellets.

29. Preparation according to claim 10, wherein the respective active ingredient contents of components (i), (ii), and (iii) are the same.

30. Preparation according to claim 10, wherein the respective active ingredient contents of components (i), (ii), and (iii) are different.

31. Preparation according to claim 1, wherein said ratio of the contents of ingredient of initial dose:first delayed-release pellet:second delayed-release pellet is about 1:2.5:4.

32. Preparation according to claim 14, wherein said capsule is a gelatin capsule.

33. Preparation according to claim 16, wherein said dose of captopril is in the range of 25 mg to 300 mg.

34. Preparation according to claim 33, wherein said dose of captopril is in the range of 50 mg to 200 mg.

35. Preparation according to claim 34, wherein said dose of captopril is in the range of 75 mg to 150 mg.

36. Pharmaceutical preparation which comprises the following components:
(i) an initial dose of an active ingredient optionally including at least one excipient,
(ii) a first delayed-release pellet, in which the active ingredient and optional excipient(s) are covered with a coating, and
(iii) a second delayed-release pellet, in which the active ingredient and optional excipient(s) are covered with a coating,
wherein the active ingredient is an ACE (angiotensin converting enzyme) inhibitor,
wherein the amounts of the coatings according to (ii) and (iii) are present in a ratio, based on weight, within the range of from 1:2 to 1:7, and
wherein the coatings according to (ii) and (iii) consist of a same coating material resistant to gastric juices.

* * * * *